(12) United States Patent
Fernandez

(10) Patent No.: US 8,202,276 B2
(45) Date of Patent: Jun. 19, 2012

(54) COPLANAR X-RAY GUIDED AIMING ARM FOR LOCKING OF INTRAMEDULLARY NAILS

(75) Inventor: Alberto Angel Fernandez, Montevideo (UY)

(73) Assignee: Synthes USA, LLC, West Chester, PA (US)

( * ) Notice: Subject to any disclaimer, the term of this patent is extended or adjusted under 35 U.S.C. 154(b) by 663 days.

(21) Appl. No.: 12/357,011

(22) Filed: Jan. 21, 2009

(65) Prior Publication Data

US 2009/0131951 A1     May 21, 2009

Related U.S. Application Data

(63) Continuation of application No. 10/947,155, filed on Sep. 23, 2004, now Pat. No. 7,481,815.

(51) Int. Cl.
*A61B 17/90*      (2006.01)
*A61B 17/58*      (2006.01)

(52) U.S. Cl. .......................................................... 606/98

(58) Field of Classification Search ............... 606/96–98
See application file for complete search history.

(56) References Cited

U.S. PATENT DOCUMENTS

| | | | | |
|---|---|---|---|---|
| 2,200,120 | A * | 5/1940 | Nauth | 606/97 |
| 4,541,424 | A * | 9/1985 | Grosse et al. | 606/98 |
| 4,865,025 | A * | 9/1989 | Buzzi et al. | 606/96 |
| 4,969,889 | A * | 11/1990 | Greig | 606/97 |
| 5,649,930 | A * | 7/1997 | Kertzner | 606/96 |
| 6,371,959 | B1 * | 4/2002 | Trice | 606/97 |
| 6,656,189 | B1 * | 12/2003 | Wilson et al. | 606/97 |
| 2005/0177175 | A1 * | 8/2005 | Johnstone | 606/130 |

* cited by examiner

*Primary Examiner* — Eduardo C Robert
*Assistant Examiner* — Mary Hoffman
(74) *Attorney, Agent, or Firm* — Fay Kaplun & Marcin, LLP

(57) ABSTRACT

A novel coplanar X-ray guided method and aiming arm device for insertion of distal locking screws in intramedullary bone nails. Radiopaque target markers in the aiming arm enable the easy positioning of an X-ray source such that an X-ray beam is coplanar with the aiming arm transverse holes. After the X-ray source is accurately oriented, a single X-ray snapshot is enough to assess the exact distortion of the implanted intramedullary nail. The X-ray beam need not be coaxial with the nail holes. The aiming arm includes a mobile portion and a fixed portion fastened to the nail, and the aiming arm can be adjusted, displacing the mobile portion over the fixed portion, to compensate for the distortion of the intramedullary nail caused by implantation in bone.

9 Claims, 14 Drawing Sheets

COPLANAR X-RAY GUIDED AIMING ARM FOR LOCKING OF INTRAMEDULLARY NAILS

PRIORITY CLAIM

The present application (a) is a Continuation Application of U.S. patent application Ser. No. 10/947,155 filed on Sep. 23, 2004 entitled "Coplanar X-Ray Guided Aiming Arm for Locking of Intramedullary Nails" and (b) has a copending related U.S. patent application Ser. No. 11/240,785 filed on Sep. 23, 2005 entitled "Coplanar X-Ray Guided Aiming Arm for Locking of Intramedullary Nails." The disclosure of these applications is incorporated herein by reference.

BACKGROUND OF THE INVENTION

The present invention is directed to aiming arm locking of intramedullary nails, and in particular to X-ray guided aiming arm locking of intramedullary nails.

It is well known the use of intramedullary nails to treat bone fractures in tubular bones. A nail is implanted in the medullary canal of the bone across the fracture site in order to retain the bone fragments on the bone nail and to secure the bone fragments from being displaced. The nail has transverse holes and is fixed to the bone by a number of locking screws or fixation bolts which must pass through holes in the nail and into the surrounding bone material. After the nail is inserted into the medullary canal, the distal end of the nail is invisible to the naked eye. Numerous methods and apparatus have been developed to successfully place locking screws across both a fractured bone and an implanted intramedullary nail.

Usually nails are locked at both ends, close to the entry point and far away from the entry point. The region of the bone where the nail is implanted is identified as proximal and the opposite end of the intramedullary nail is distal. Nail locking is currently made using either mechanical aiming arms or X-ray guidance.

Mechanical aiming instruments, which are fixedly attached to the proximal end of the implanted bone nail, may provide concentric alignment with the proximal screw holes in order to enable reliable drilling such as those disclosed in U.S. Pat. Nos. 5,334,192, 5,766,179, and 6,514,253.

An advantage of this mechanical aiming arm is that neither the patient nor the surgeon will be exposed to X-ray source. However, distal screw holes may not perform satisfactorily due to distortion of the intramedullary nail while being driven into the bone and/or mechanical stress on the aiming arm. Aiming-arm-guided-locking is usually successful for proximal locking since the distortion of the nail while inserted into the bone is negligible for a short length of nail. However, it is usually not successful for distal locking except for very short nails since the distortion of the nail while inserted into the bone is not negligible.

Distortion in the implanted intramedullary nail happens in the 3D space and can be analyzed into its main components:
  Length variation in the axis of the intramedullary nail.
  Rotational distortion in the axis of the intramedullary nail.
  Flexion distortion in the plane of the intramedullary nail distal holes
  Flexion distortion perpendicular to the plane of the distal holes of the intramedullary nail.

We can accept, when using non slotted intramedullary nails provided of coplanar distal holes, that the first three mentioned distortions: length distortion in the axis of the nail, rotational distortion in the axis of the nail, and flexion deformity in the plane of the distal screw holes of the nail, are negligible for our task of distal locking. However, flexion distortion in a plane perpendicular to the plane of the distal screw holes of the nail is very important and the one that concerns when distal locking is the subject of matter.

X-ray guidance is what is presently most used for distal locking except for very short nails. The procedure starts by exactly positioning the X-ray beam in the axis of the nail holes, something that is not always straightforward for the X-ray technician. The intramedullary nail will cast a dark, elongate image on the X-ray monitor, while the nail holes will appear as light circles or ovals. In particular, the nail hole will appear as a circle when the X-ray source is positioned such that the X-ray beam is parallel to the axis of the nail hole, something that is a complex 3D procedure.

After the nail holes have been located, a drill is used to drill through the bone for insertion of the locking screw. This procedure may be accomplished either with or without the use of an aiming arm guide, wherein said aiming arm guide can be fastened to the bone nail or not.

Various aiming guides are already known in the art to be used in conjunction with the X-ray source in order to accurately place the locking bone screws across both a fractured bone and an implanted intramedullary nail, such as those disclosed in U.S. Pat. Nos. 4,803,976, 4,850,344, 6,656,189, 4,667,664, and 4,881,535.

All these X-ray guided procedures require the X-ray source positioned such that the X-ray beam is parallel to the axis of the nail hole. This is not always simple, and sometimes not even possible. It may also increase undesirable X-ray exposure to the surgeon, patient and operating room staff, and lengthen the surgical procedure.

Attempts have been made in the past to obtain a successful method for distal locking, which overcome the problems associated with X-ray guided locking. However, most of these systems are cumbersome and require additional bone screw holes in order to exactly assess the position of the hole in the distorted intramedullary nail after implanted into the bone.

The present invention relates to a novel apparatus and method of distal locking that allows the surgeon to target and install bone screws into an intramedullary nail in an accurate, fast and reliable manner.

BRIEF SUMMARY OF THE INVENTION

Is therefore an object of the present invention to provide an aiming arm capable of being adjusted to compensate for the intramedullary nail distortion after its insertion into the bone, making use of the information given by a few snap shots of the X-ray image intensifier.

Another object of the present invention is to provide a radiolucent aiming arm for distal locking of an intramedullary nail provided of radiopaque target markers capable to determine when the position of an X ray source is such that an X ray beam is coplanar with the aiming arm holes axis.

Further, it is an object of the present invention to reduce undesirable X-ray exposure to the surgeon, patient and operating room staff.

The present invention by being an easy and straightforward procedure for the X-ray technician and the surgeon makes distal bone fixation of intramedullary nails simple and fast overcoming one of the most important subject of matter of actual surgery, time shortening.

The aiming arm of the present invention overcomes the disadvantages of conventional aiming arms by providing an easy obtainable X-ray guidance for distal locking without the requirement of the X-ray beam to be coaxial with the nail hole, so that reducing undesirable X-ray exposure to the surgeon, patient and operating room staff.

The novel feature of the present invention is an aiming arm capable of being adjusted to compensate for the nail deformation after its insertion into bone, making use of the information given by a few snap shots of the X-ray image intensifier.

By fulfilling the recently mentioned objects, the present invention is extremely helpful to the medical care area.

The preferred embodiment of the present invention provides an adjustable aiming arm fastened to a bone nail. The aiming arm is constructed of a radiolucent material and has coplanar transverse holes or apertures. The aiming arm has a number of radiopaque target markers to enable the X-ray technician to assess when the position of an X-ray source is such that an X-ray beam is coplanar with the transverse holes of aiming arm. The image shown by a single X-ray snapshot in this position gives the surgeon precise information on the amount of nail distortion after nail insertion into the bone, so that allowing the surgeon to determine the aiming arm adjustment needed to compensate for the distortion of the intramedullary nail. Once the aiming arm is accurately oriented over the nail hole, so as the aiming arm transverse holes are coaxial with the nail holes, the surrounding bone material can be drilled. After the bone is drilled, locking bone screws are screwed through the protective sleeves previously inserted into the aiming arm transverse holes.

Other objects, advantages and novel features of the present invention will become apparent from the following detailed description of the invention when considered in conjunction with the accompanying drawings.

BRIEF DESCRIPTION OF THE SEVERAL VIEWS OF THE DRAWINGS

Preferred features of the present invention are disclosed in the accompanying drawings, wherein similar reference characters denote similar elements throughout the several views, and wherein.

DETAILED DESCRIPTION OF THE INVENTION

Hereinafter, a method of bone fixation according to the preferred embodiment of the present invention will be explained with reference to FIGS. 1-7.

Figure 1:
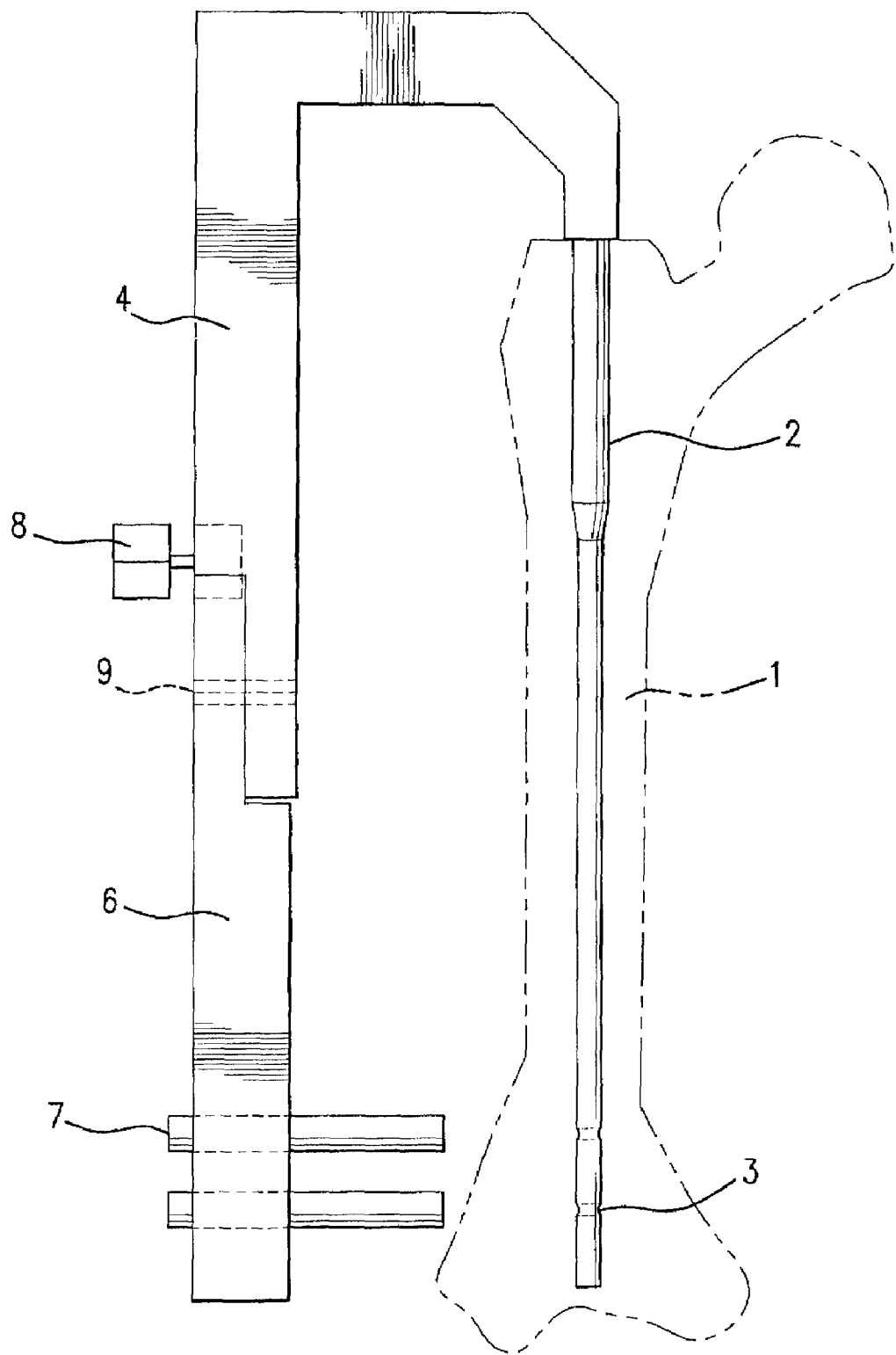
FIG. 1 shows a plan view of the aiming arm according to the present invention wherein the protective sleeves and a fastened intramedullary nail are shown.

Referring to FIG. 1 there is shown an aiming device 4, on which is mounted a mobile aiming arm portion 6. An intramedullary nail 2, with two coplanar transverse holes 3 is fastened to the aiming arm 4. Protective sleeves 7 slide through holes 5 located in the mobile part of the aiming arm 6, guiding drills and bone screws through the nail transverse holes 3 for distal locking of the intramedullary nail 2. Mobile part rotates about the axis 9 over aiming arm.

Figure 2:
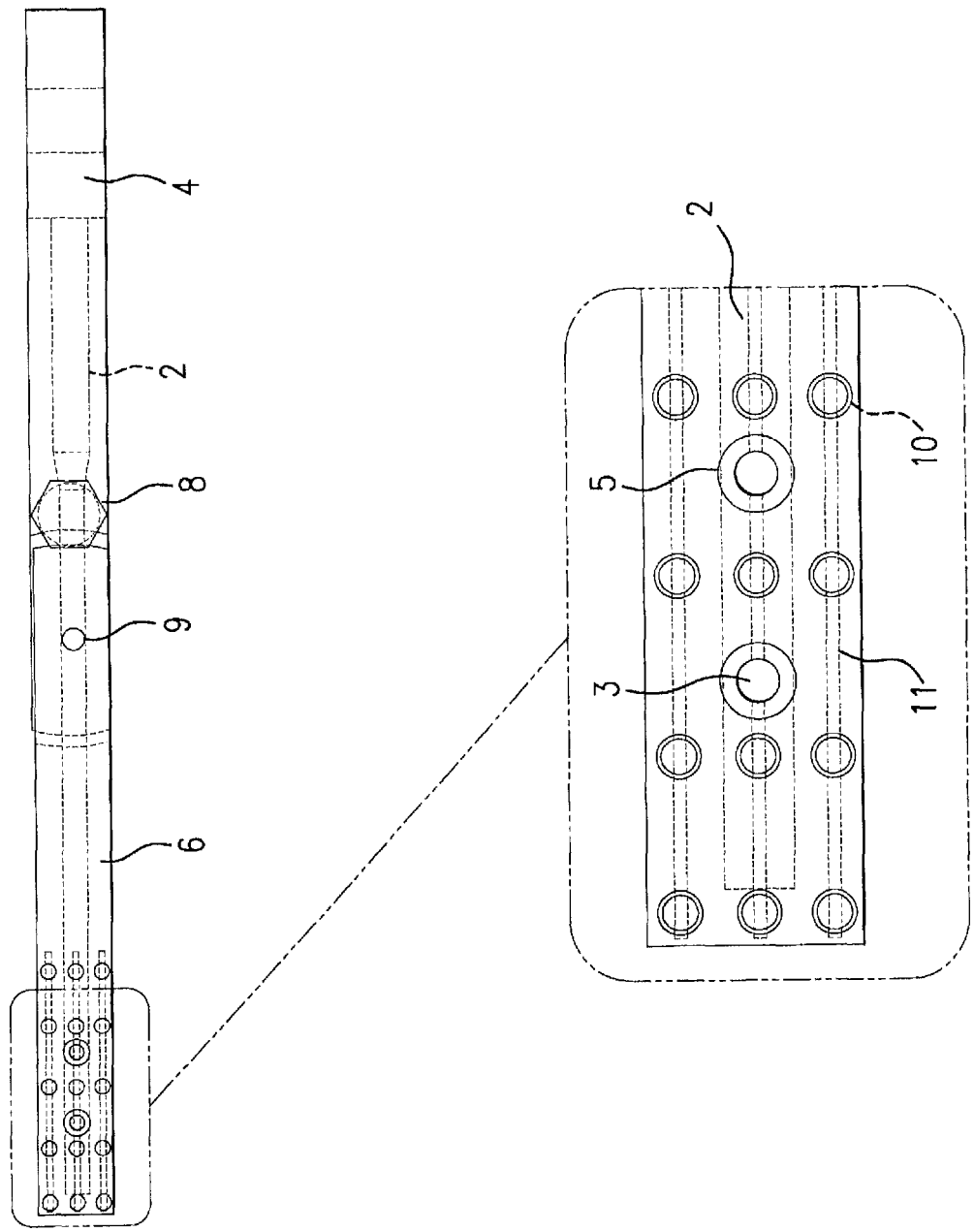
FIG. 2 is a side view illustrating the aiming arm transverse holes precisely aligned with the intramedullary nail holes.
Figure 3:
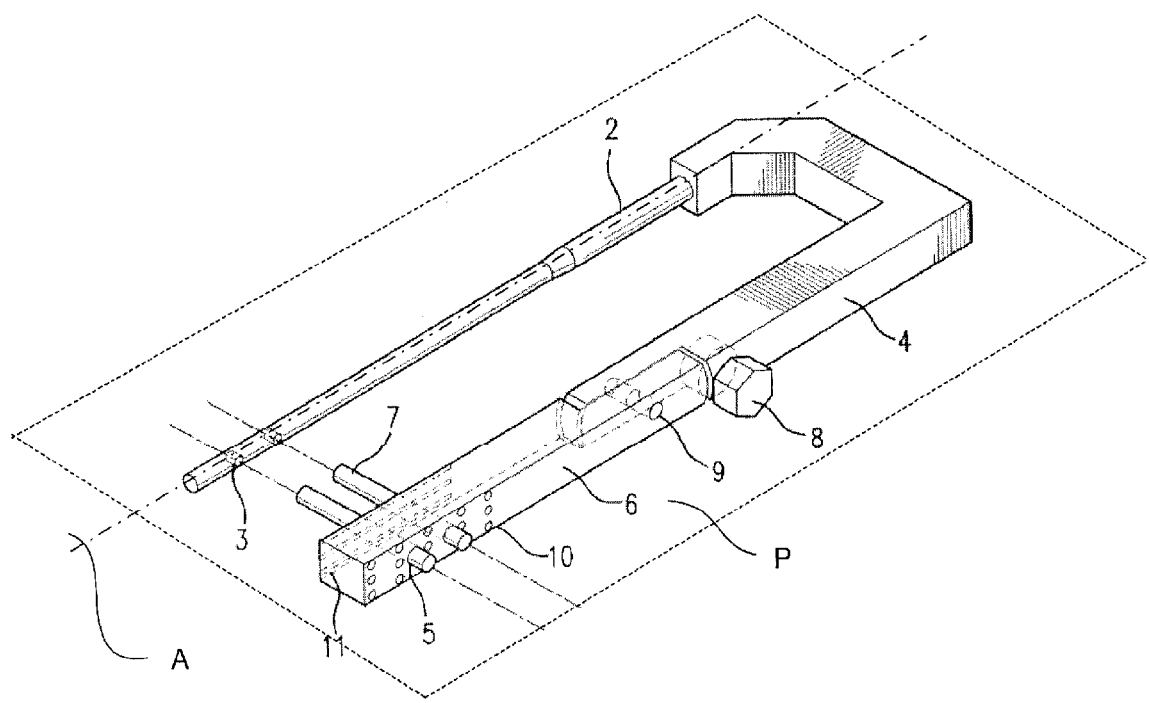
FIG. 3 shows a perspective view of the aligned aiming arm according to the present invention, wherein the protective sleeves and the intramedullary nail fastened to the aiming arm are shown.

The aiming arm 4 is fastened to the intramedullary nail 2, and before the nail 2 is inserted into the bone 1, aiming arm holes 5 and intramedullary nail holes 3 are precisely aligned as shown in FIGS. 2 and 3. Plane P defined by the longitudinal axis A of intramedullary nail 2 and the axis of the aiming arm transverse holes 5 is shown in FIG. 3.

Figure 4:
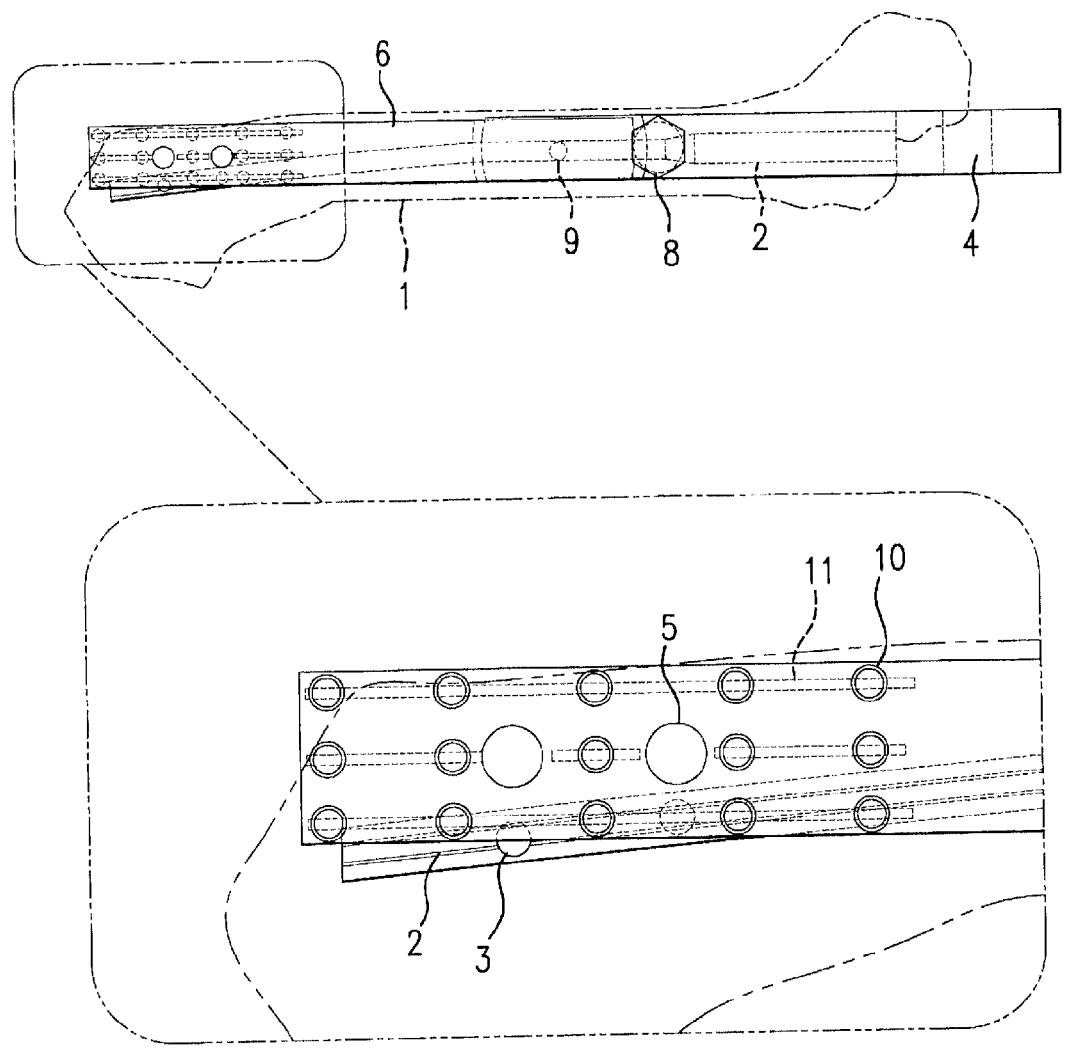
FIG. 4 shows a side view of the aiming arm according to the present invention, wherein the fastened intramedullary nail is distorted after bone insertion, and wherein aiming arm holes and intramedullary nail transverse holes are not aligned thereof.

After implanted, the distortion of the intramedullary nail causes aiming arm holes 5 and intramedullary nail holes 3 non-alignment as shown in FIG. 4.

Figure 6:
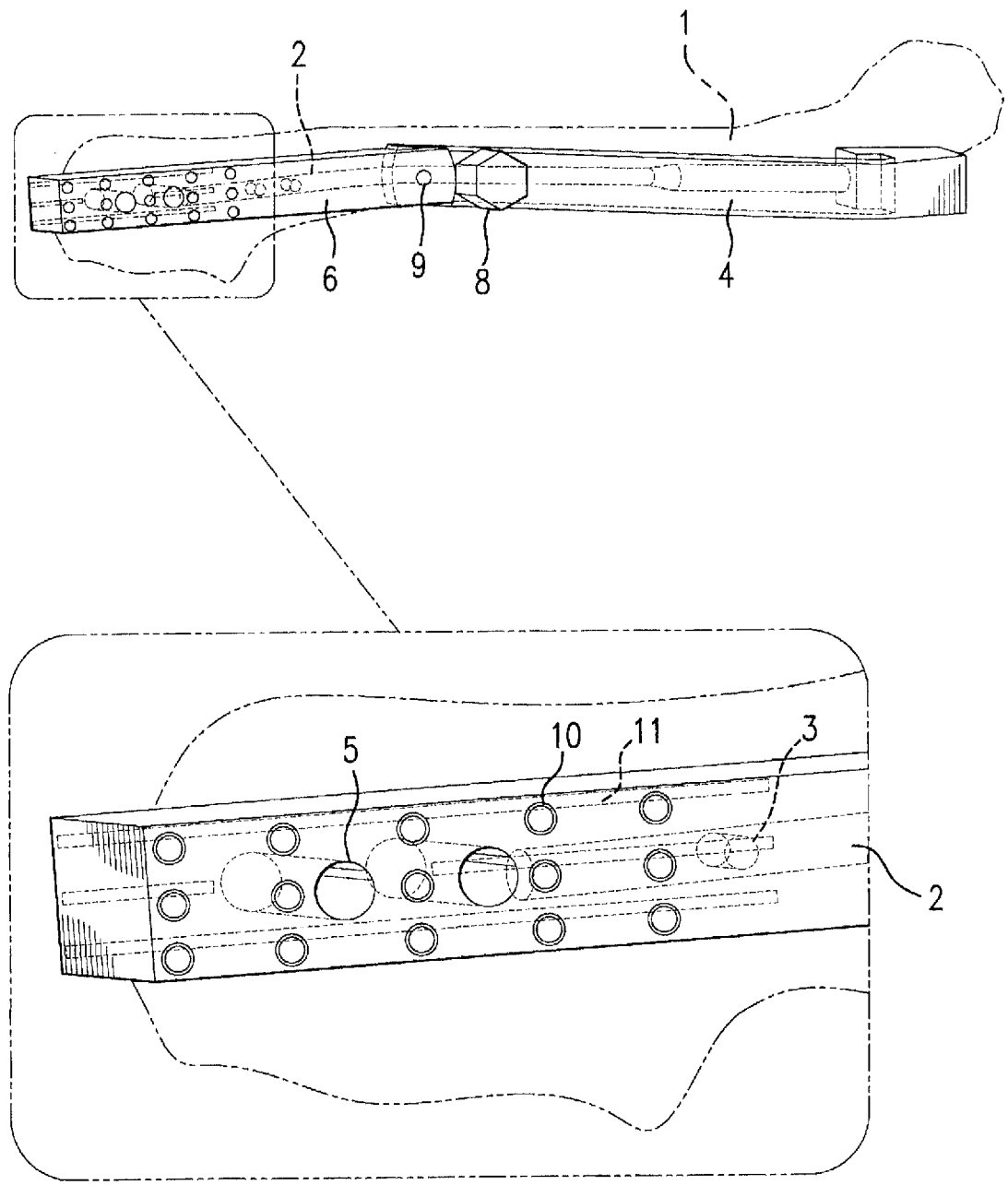
FIG. 6 is a perspective view in the plane of the aiming arm holes, illustrating how the alignment of intramedullary nail cross holes and aiming arm holes can be confirmed despite the fact that the X-ray beam is not aligned with the axis of the intramedullary nail holes.

The aiming arm 4 is mostly made of a relatively radiolucent material and is provided with radiopaque target markers 10, 11, which enable a surgeon to assess when the position of the X ray source is such that an X-ray beam is coplanar with the plane of the aiming arm holes, not being necessary for the X ray beam to be coaxial with the intramedullary nail holes 3. As a consequence, a single snapshot of an X ray source positioned such that an X ray beam is coplanar with the aiming arm holes 5 is enough to determine the exact distortion of the intramedullary nail 2, as shown in FIG. 6.

Figure 5:
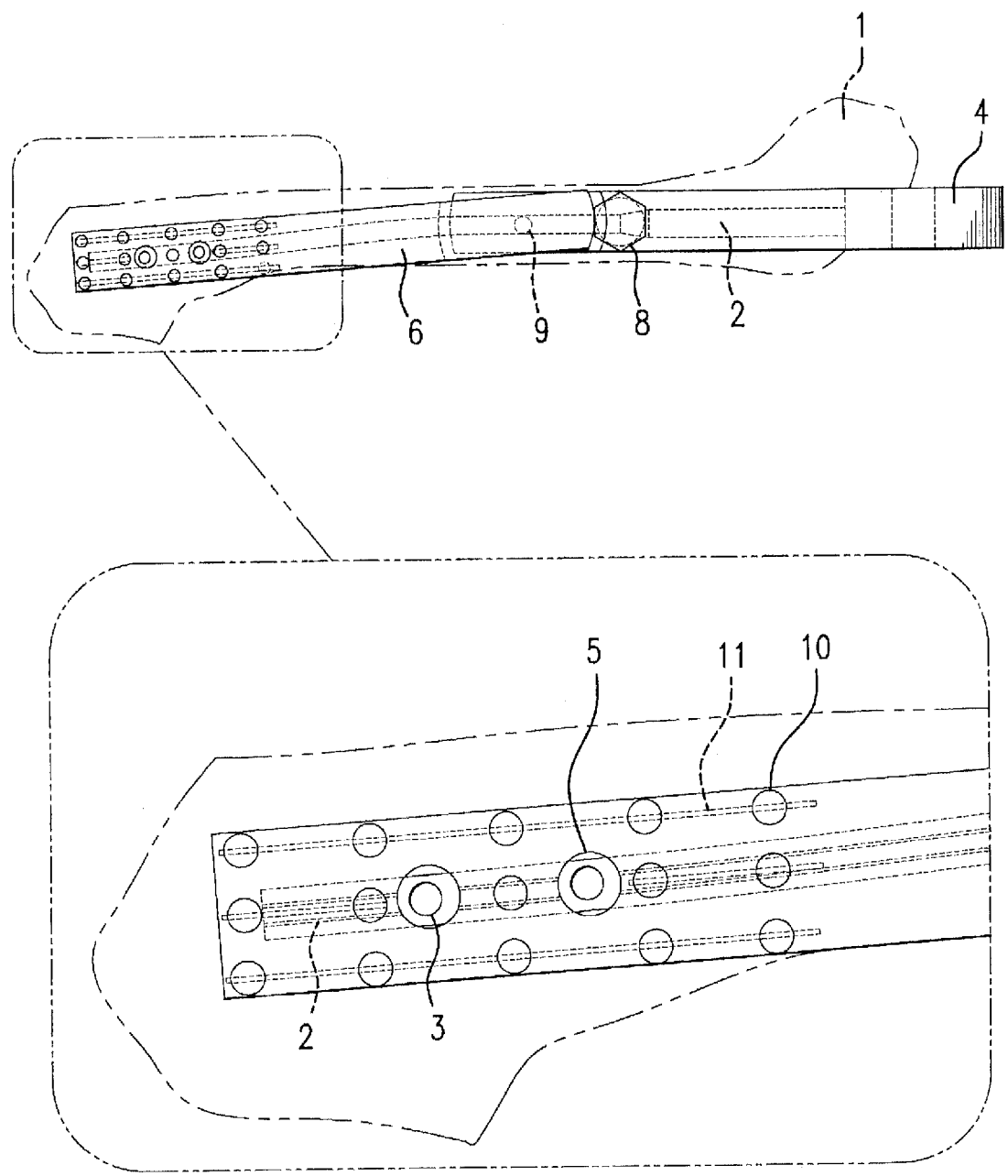
FIG. 5 shows a side view of the aiming arm according to the present invention after compensation for the nail deformation was made, so that aiming arm holes and intramedullary nail transverse holes are aligned.
Figure 7:
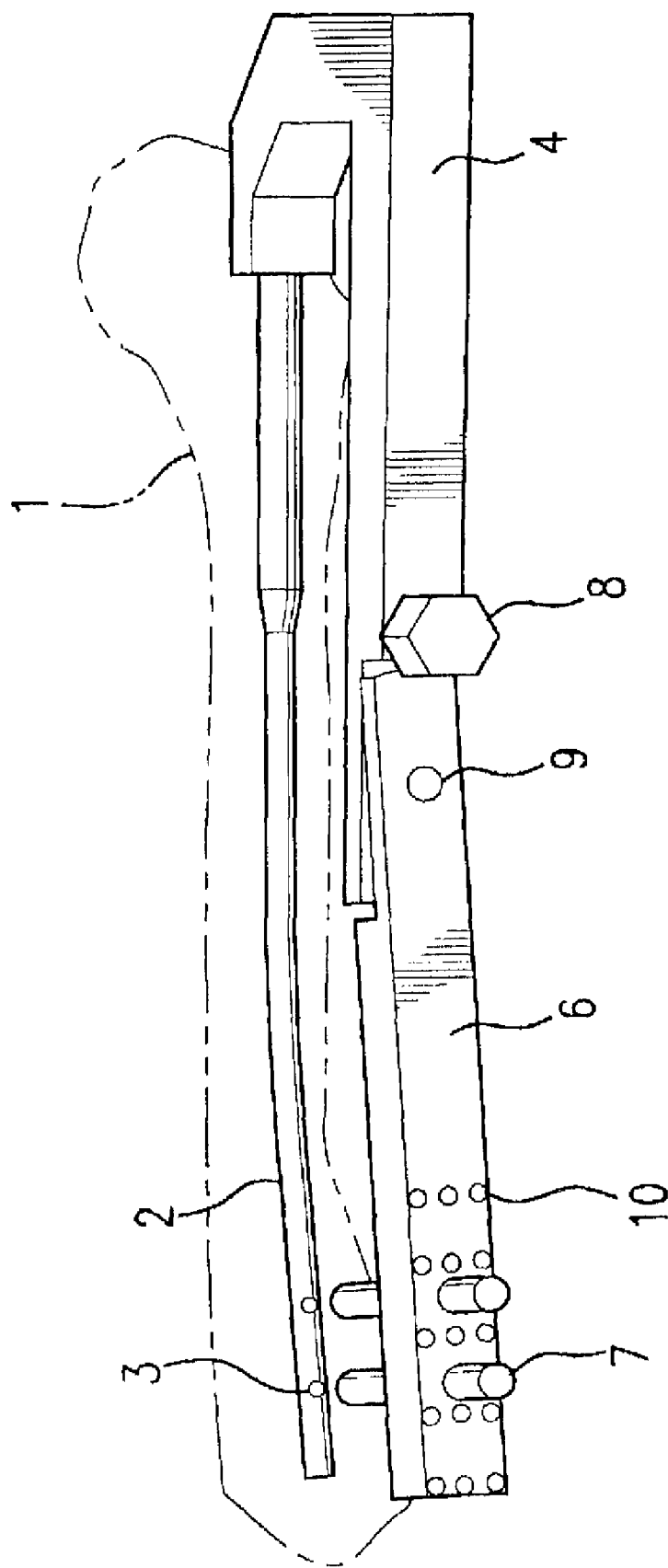
FIG. 7 shows a perspective view of FIG. 5.

By turning the adjusting knob 8 the required amount, the mobile part of the aiming arm 6 can be positioned to compensate for the distortion of the intramedullary nail 2, so that aiming arm holes 5 and nail holes 3 are re-aligned as shown in FIGS. 5 and 7.

Once aiming arm holes 5 and intramedullary nail holes 3 are aligned it is easy to slide in the protective sleeves 7 through the aiming arm holes 5. After the protective sleeves 7 are positioned, a drill bit is aligned with the nail hole 3 and drilled through the nail hole 3 and the surrounding bone material. Once the second drill bit is drilled accurately through the second nail hole 3 and the surrounding bone material, the second drill bit is removed, and a locking screw is inserted through the protection sleeve and screwed through the bone and second nail hole 3 to secure the nail to the bone. Finally, the first drill bit is removed, and a second locking screw is inserted through the sleeve 7 and screwed through the bone 1 and first nail hole 3 to secure the intramedullary nail 2 to the bone 1.

Next, an aiming arm device according to the second embodiment of the present invention will be explained with reference to FIGS. 8-14.

Figure 8:
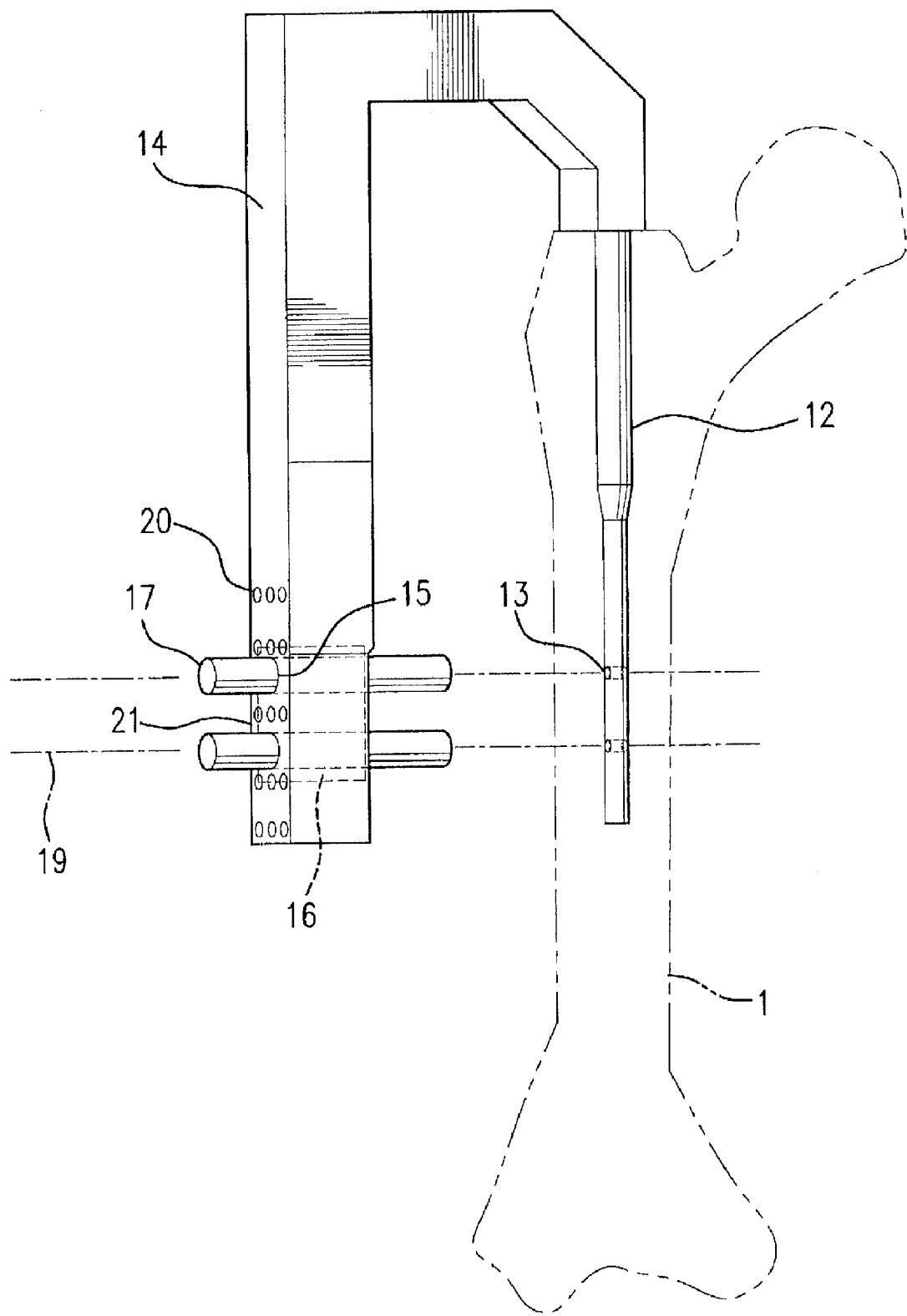
FIG. 8 shows a perspective view of the aiming arm according to the present invention wherein a fastened short intramedullary nail implanted into the bone is shown.
Figure 9:
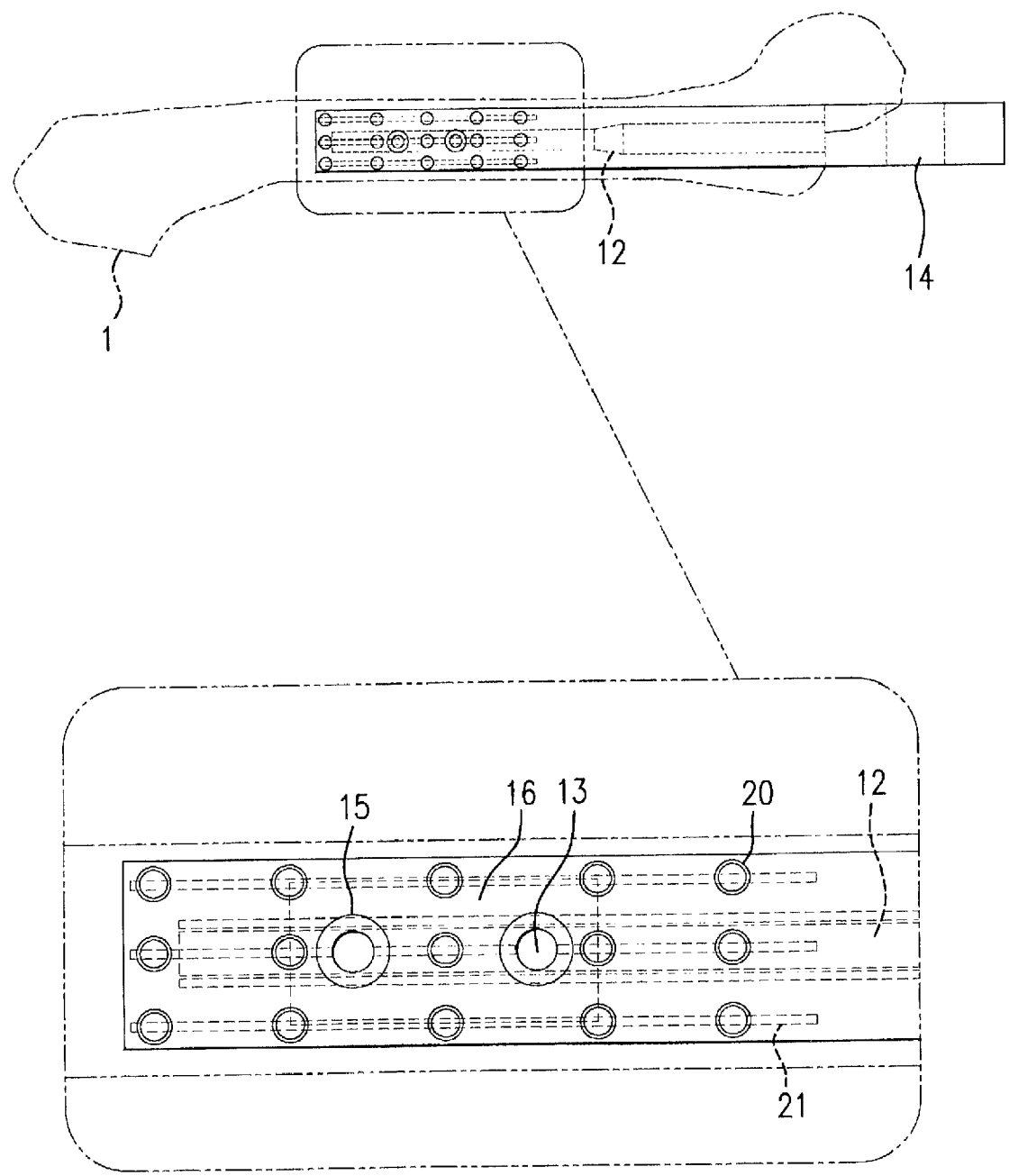
FIG. 9 is a side view illustrating the aiming arm holes precisely aligned with the short intramedullary nail.
Figure 10:
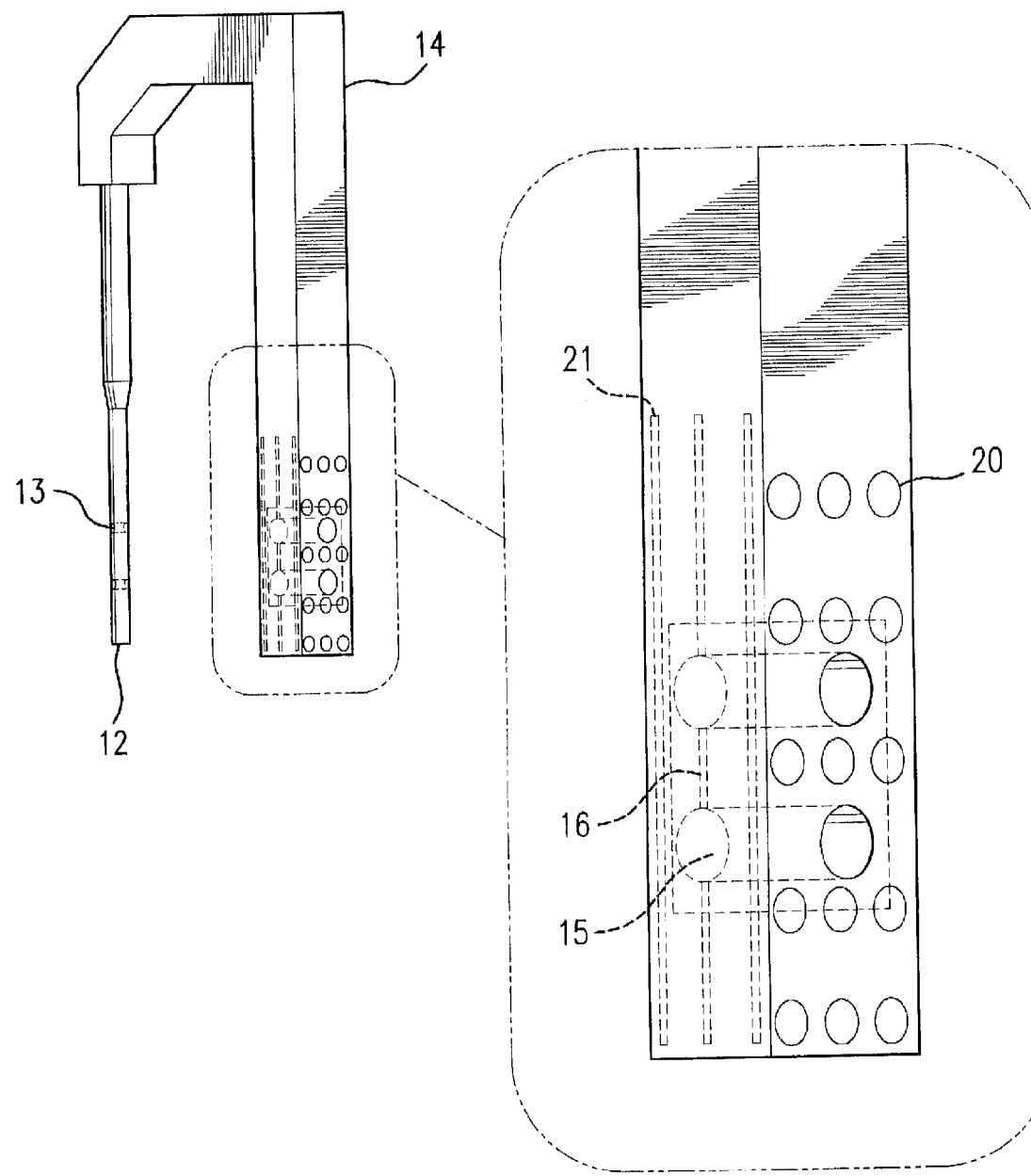
FIG. 10 shows a perspective view of FIG. 9, wherein the protective sleeves, the short intramedullary nail fastened to the aiming arm and the front and rear radiopaque markers are shown.

Referring to FIG. 8 there is shown an aiming device 14, fastened to a short intramedullary nail 12. The intramedullary nail 12 is provided with two coplanar transverse holes 13. Protective sleeves 17 can slide through holes 15, existing in the insert 16 situated in the aiming arm 14 in order to guide drills and bone screws through the nail cross holes 13, for distal locking of the intramedullary nail 12. Insert holes 15, and nail holes 13 have the same axis 19.

The aiming arm 14 provided of radiopaque target markers, bubbles 20 and lines 21, is fastened to the bone nail 12. Before the intramedullary nail 12 is inserted into bone 1, aiming arm holes 15 and nail holes 13 are perfectly aligned as it can be seen in FIGS. 9 and 10.

Figure 11:
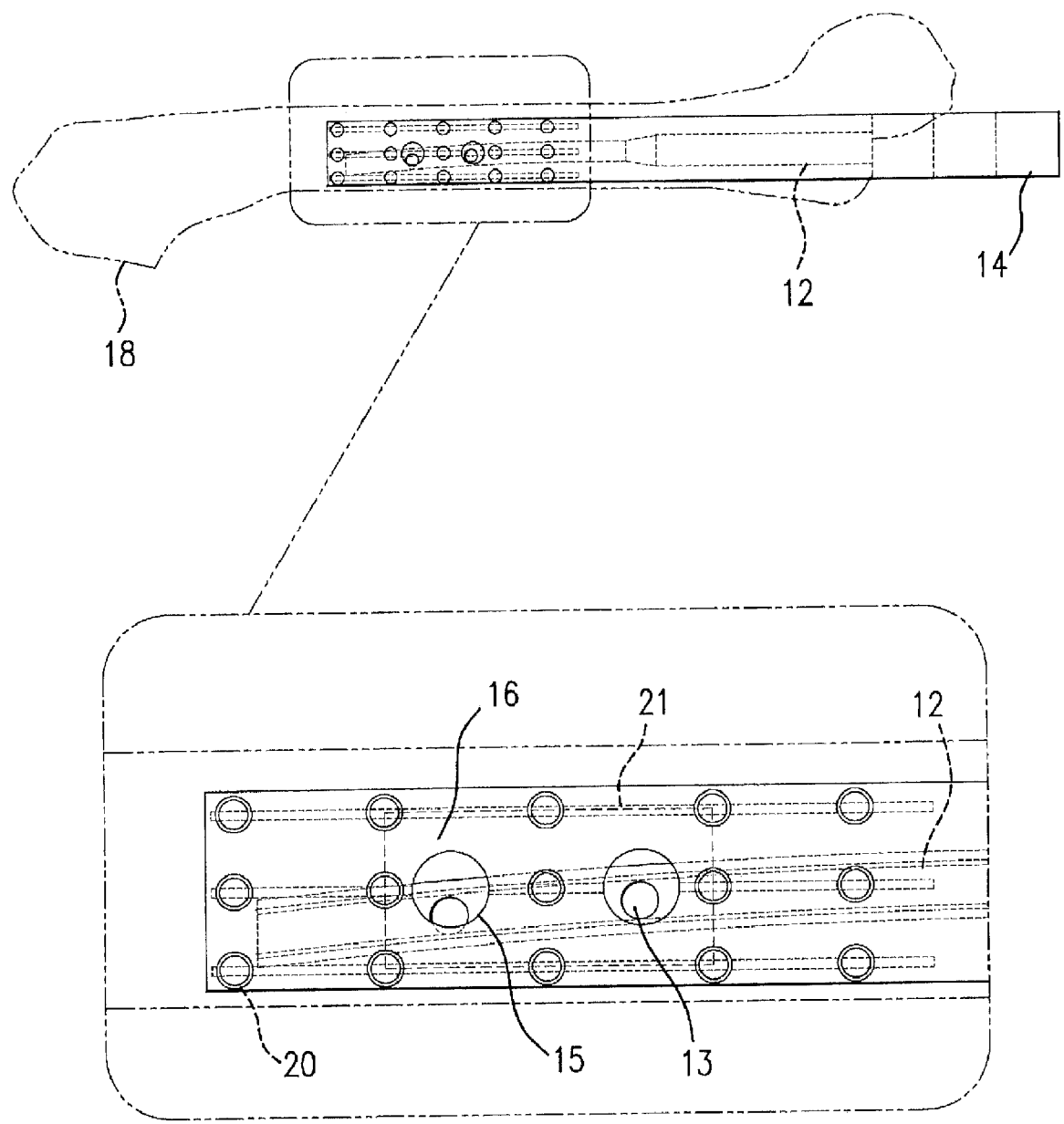
FIG. 11 shows a side view of the aiming arm according to the present invention, wherein the fastened intramedullary nail is distorted after bone insertion, and wherein aiming arm holes and intramedullary nail transverse holes are not aligned thereof.

After bone insertion the intramedullary nail 12 commonly distorts such that aiming arm holes 15 and nail holes 13 are not aligned anymore as shown in FIG. 11.

Figure 12:
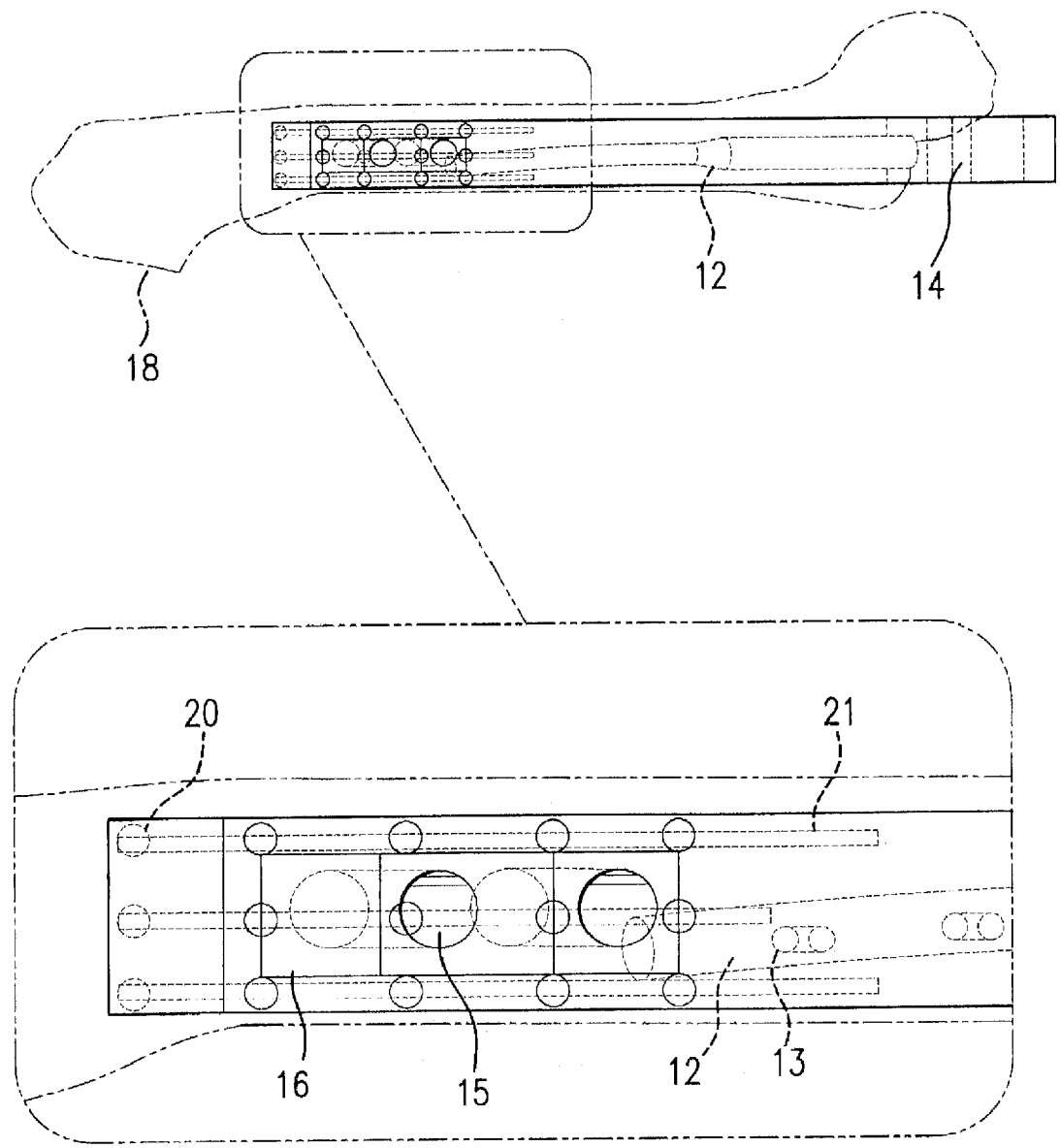
FIG. 12 is a perspective view in the plane of the aiming arm holes, illustrating how a single X-ray snapshot in this plane enables to assess the exact distortion of the intramedullary nail after inserted into the bone.

A single snapshot of an X ray source positioned such that an X ray beam is coplanar with the aiming arm holes 15 is enough to determine the amount of nail distortion, as shown in FIG. 12.

Figure 13:
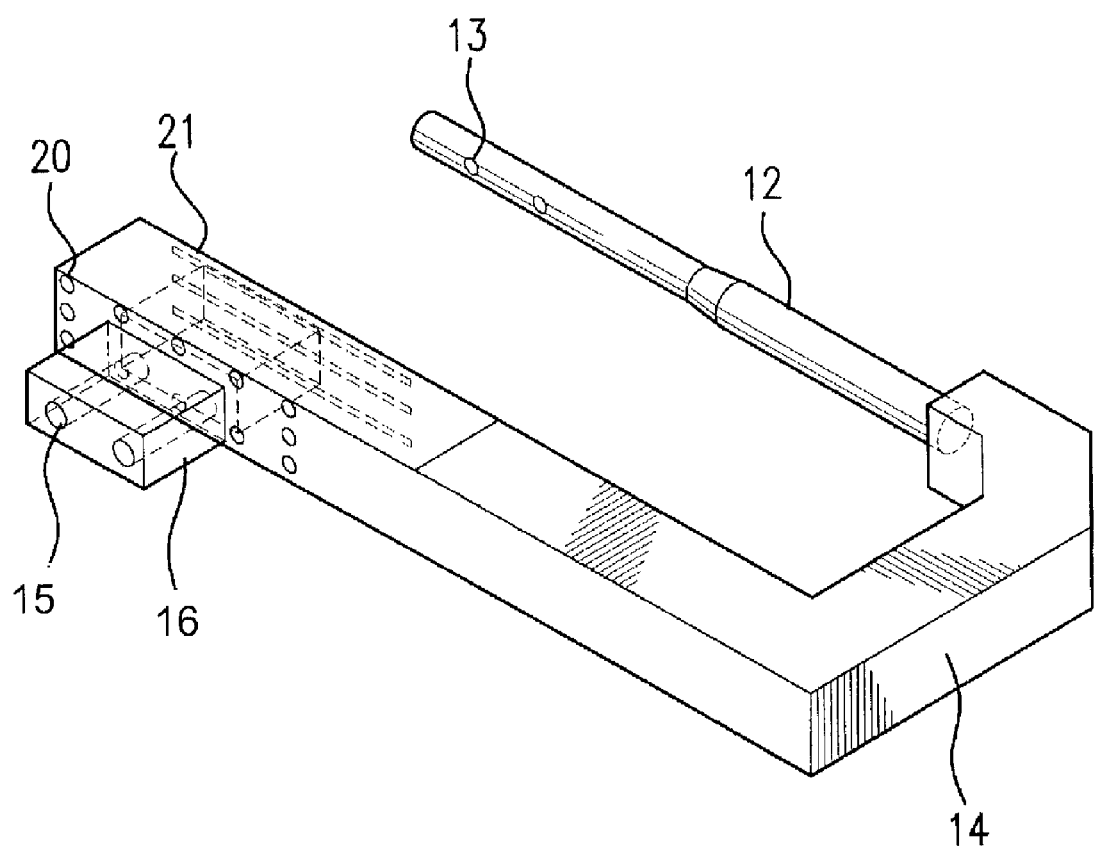
FIG. 13 shows a perspective view of the aiming arm according to the present invention wherein the distorted intramedullary nail, and an insert with offset holes to compensate for the distortion of the intramedullary nail are shown.
Figure 14:
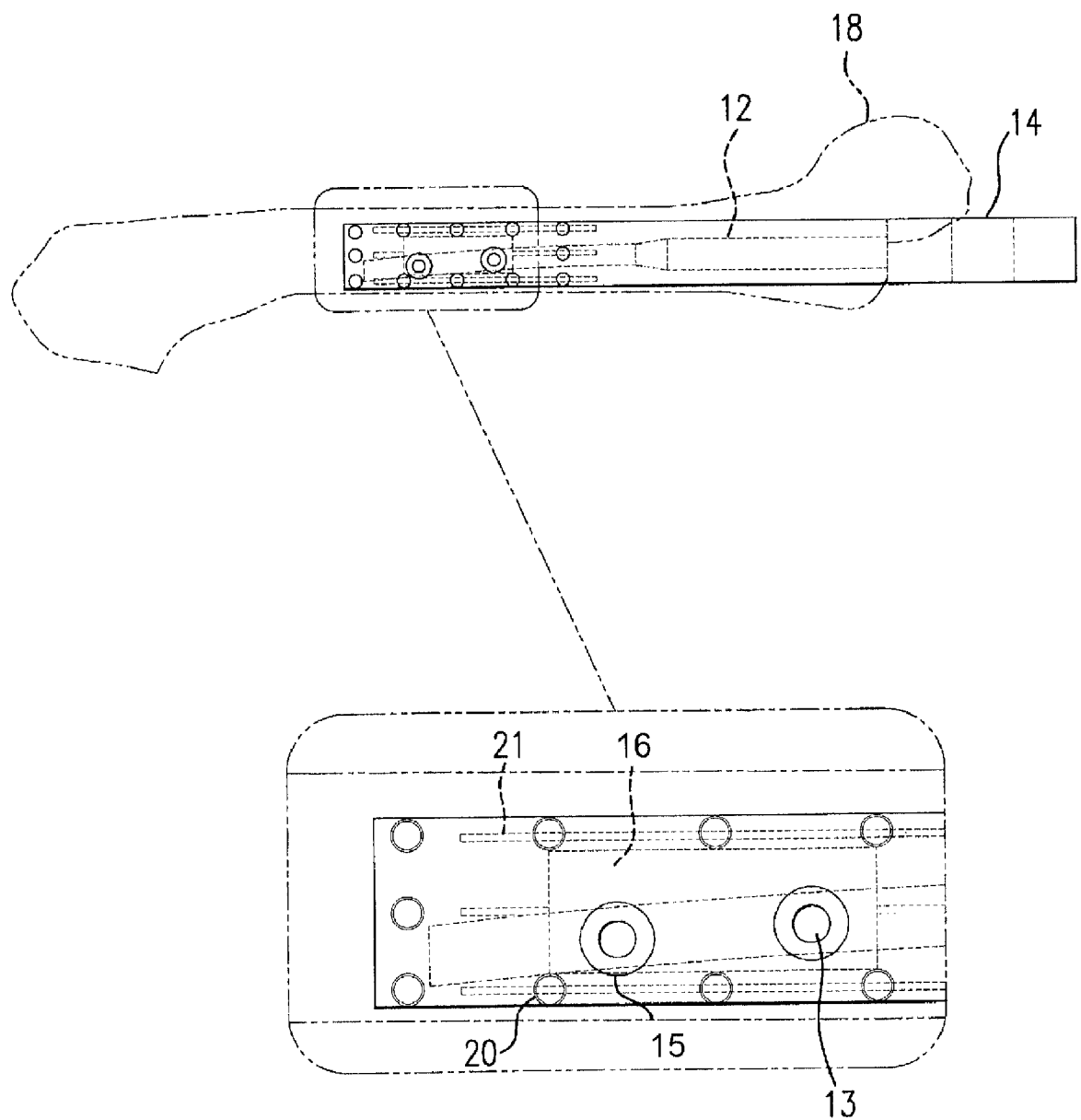
FIG. 14 shows a side view of FIG. 13.

By using an insert 16, provided with offset holes, aiming arm holes 15 and intramedullary nail holes 13 can be aligned again as shown in FIGS. 13 and 14.

Once aiming arm holes 15 and intramedullary nail holes 13 are aligned it is easy to slide in the protective sleeves 17 through the aiming arm holes 15, to slide in through the protective sleeves 17 the drill to bore the bone 1, and to slide in through the protective sleeve 17 the bone screw which will match the nail hole 13 as it is required to lock the intramedullary nail 12.

While I have illustrated and described two preferred embodiments of the invention, it will be understood that those skilled in the art will thereby be enabled to devise variations and modifications without departing from the spirit and scope of this invention, as defined in the appended claims.

What I claim as my invention is:

1. A radiolucent aiming arm for determining the location of at least one transverse hole in an implanted intramedullary nail, comprising:

an elongated body constructed substantially of radiolucent material, the elongated body having a first end configured and adapted for releasable attachment to a proximal end of the intramedullary nail;

an insert removably inserted into an opening of the elongated body, the insert including a front surface, a back surface, and at least one transverse hole intersecting the front and back surfaces and defining a central hole axis, wherein the at least one transverse hole of the insert is axially aligned with the at least one transverse hole in the intramedullary nail; and a first radiopaque marker positioned on a portion of the front surface and a second radiopaque marker positioned on a portion of the back surface, the first radiopaque marker having a different shape than the second radiopaque marker.

2. The radiolucent aiming arm of claim 1, wherein the first and second radiopaque target markers are configured and dimensioned to indicate that an X-ray beam is coplanar with a plane defined by the central hole axis and a second longitudinal axis of the intramedullary nail, prior to any distortion caused by insertion of the nail into bone.

3. The radiolucent aiming arm of claim 1 wherein: the elongated body includes a first part configured and adapted for releasable attachment to the proximal end of an intramedullary nail and a second part containing the opening for receiving the insert.

4. The radiolucent aiming arm of claim 2, wherein the at least one target marker positioned on the front surface is at least one of the group consisting of a circle and a line, and the at least one target marker positioned on the back surface is at least one of the other of the group consisting of a circle and a line.

5. The radiolucent aiming arm of claim 1, wherein the at least one transverse hole on the insert includes a plurality of offset holes with an orientation that matches an orientation of corresponding transverse holes in the intramedullary nail after a distortion occurs in the intramedullary nail.

6. The radiolucent aiming arm of claim 5, wherein the plurality of offset holes are structured to accommodate sleeves.

7. The radiolucent aiming arm of claim 5, wherein the offset holes are coaxial with the corresponding offset holes in the intramedullary nail when the insert is inserted in the opening of the elongated body.

8. The radiolucent aiming arm of claim 1, wherein the elongated body is adjustable to intramedullary nails of different lengths.

9. The radiolucent aiming arm of claim 2, wherein the at least one target marker positioned on the front surface includes at least three circles and the at least one target marker positioned on the back surface includes at least one straight line.

* * * * *